United States Patent
Hell

(10) Patent No.: US 6,377,040 B1
(45) Date of Patent: Apr. 23, 2002

(54) EDDY CURRENT PROBE AND PROCESS FOR CHECKING THE EDGES OF METAL ARTICLES

(75) Inventor: Ludwig ter Hell, Kirchseeon (DE)

(73) Assignee: Pruftechnik Dieter Busch AG, Ismaning (DE)

( * ) Notice: Subject to any disclaimer, the term of this patent is extended or adjusted under 35 U.S.C. 154(b) by 0 days.

(21) Appl. No.: 09/360,642

(22) Filed: Jul. 26, 1999

(30) Foreign Application Priority Data

Jul. 24, 1998 (DE) .......................................... 198 33 276

(51) Int. Cl.⁷ .............................................. G01N 27/82
(52) U.S. Cl. ........................................ 324/240; 324/242
(58) Field of Search ................................ 324/240, 228, 324/239, 242, 243, 260, 262, 241; 336/188, 84 R

(56) References Cited

U.S. PATENT DOCUMENTS

| | | | |
|---|---|---|---|
| 4,016,487 A | * 4/1977 | Neumaier | ..................... 324/37 |
| 4,274,054 A | 6/1981 | Savidge et al. | |
| 4,445,089 A | * 4/1984 | Harrison | ..................... 324/238 |
| 4,625,165 A | * 11/1986 | Rothstein | ..................... 324/220 |
| 5,130,652 A | 7/1992 | Kawakami et al. | |
| 5,617,024 A | 4/1997 | Simpson et al. | |
| 5,648,721 A | 7/1997 | Wincheski et al. | |

* cited by examiner

Primary Examiner—Jay Patidar
(74) Attorney, Agent, or Firm—Nixon Peabody LLP; David S. Safran

(57) ABSTRACT

An eddy current-based test probe is used for checking especially the edges of rolled steel rods. It detects defects both in the transverse and also the longitudinal direction of these rods. The probe has a combination of several coils with which magnetic flux differences can be detected. The simultaneous sensitivity of the probe in the transverse and longitudinal directions of the test specimen is induced by its executing rotary motion around its vertical axis. An electrical induction motor is used as the drive for rotary motion. The electrical feed and receiving signals of the probe system are coupled and decoupled without contact via a rotary transformer.

7 Claims, 4 Drawing Sheets

EDDY CURRENT PROBE AND PROCESS FOR CHECKING THE EDGES OF METAL ARTICLES

BACKGROUND OF THE INVENTION

1. Field of the Invention

The invention relates to an eddy current test probe for testing metal articles.

2. Description of Related Art

Test instruments of the type to which the invention is directed have been known for some time and are used especially to test tubular articles from their inside or outside. Other important applications of these devices relate to checking of rolled sheets, rods or wires in the metalworking industry. Diverse efforts have been made, especially, to inspect the periphery of rods, tubes or wires on all sides. To do this, test probes are used which are guided around these articles with a mechanically driven device and with high speed in order to continually carry out eddy current tests. At the same time, and with a stipulated linear speed, the workpiece to be examined is moved through this test means. The material faults to be detected are of a varied nature. They can either be extremely visible, or can be located within the material. They can be punctuate or can have an extended, especially oblong shape. Depending on which of these prerequisites are present, an eddy current test probe can have a more or less high detection efficiency. But again, it has been established that detection of defects on the edges of metal rods with a roughly rectangular cross section (billets, slabs) is extremely difficult and usually imperfect. This relates especially to the problem formulation when defects can occur, at the same time, in the longitudinal direction and the transverse direction of these rods and are to be detected with high reliability. Conventionally, the problem is additionally exacerbated by the fact that the cross sectional dimension of these products can be subject to slight variations without edge defects actually being present.

An attempt to solve the above problem is described in U.S. Pat. No. 5,130,652; compare FIGS. 1,3, 4 and 5 there. The field coils there are not only large, unwieldy and expensive, but due to their volume can only be operated with direct or low frequency alternating current. The known advantages of high frequency testing based on eddy currents thus cannot be observed there. A similar approach is followed in the invention described in U.S. Pat. No. 5,648,721. As in the approach in U.S. Pat. No. 5,130,652, due to the circling motion of the probe in edge testing, however, the disadvantage arises that material areas of interest, then adjacent material areas are alternately checked. Accordingly, the invention according to U.S. Pat. No. 5,648,721 is mainly intended also for checking of rivets and screws on aircraft.

In U.S. Pat. No. 5,617,024, derived from the same invention as U.S. Pat. No. 5,648,721, test probes are presented which are only of a rather general nature and are not suited for simultaneously discovering transverse and longitudinal faults on the edges of rod-shaped articles of metal or an electrical conductor. Another probe guided on an arc for checking flat metal pieces is described in U.S. Pat. No. 4,274,054. As is described there, the proposed rotating coil arrangement is, however, unsuited for checking edges of the test specimens to be examined since another approach with nonrotating probes is presented for checking of edges.

SUMMARY OF THE INVENTION

The primary object of the invention is in making available an economical, very reliable test instrument which is easy to operate and which is especially suited to the detecting of defects on or near the edges of polygonal metal rods, and at the same time, is able to detect defects in at least the longitudinal and transverse direction of these rods. In addition, as much as possible, defects should also be detectable which have an angular position between these directions. Moreover, the test instrument or a corresponding probe (without modifications) should also be usable for material tests on flat metal articles.

This object is achieved by a test probe for nondestructive material testing and for detecting inhomogeneities or defects of an article of conductive material which has a instrument transformer, optionally one or more measurement oscillators, with an impedance or reactance which changes when these material defects are present, at least changes differentially. Especially in an embodiment with a instrument transformer, it is provided that one or more transmitting (primary) and receiving (secondary) coils, connected as instrument transformers and supplied with a high frequency voltage, are used to acquire magnetic fluxes or partial fluxes produced as eddy current, the instrument transformer being able to detect differences of partial magnetic fluxes which are generated by the instrument transformer in a metal test specimen and are emitted by it, and the instrument transformer having at least one axis of symmetry. In accordance with the invention, the transformer is continuously turned around a preferred axis of the axes of symmetry, especially the vertical axis. In doing so, the instrument transformer executes rotary motion relative to the test specimen (or vice versa). This axis of symmetry, in accordance with the invention, is thus oriented essentially perpendicular to the surface of a metal test specimen or points at its longitudinal axis. The rotary motion of the instrument transformer is best effected mechanically, i.e., preferably by means of an electric motor drive.

In the embodiment according to the invention with an instrument transformer, this object is therefore achieved in a special way by a test probe for nondestructive material testing and detecting inhomogeneities or defects of an article of a conductive material being prepared which can produced eddy currents in the material to be tested and which can detect them (by the correspondingly emitted eddy magnetic fields) and has the following features:

The test probe is equipped with one or more transmitting coils with longitudinal axes oriented essentially perpendicularly to the surface of the article to be tested or at least aligned such that a surface normal of the article on an area to be tested points in the parallel direction to the longitudinal axis of one such transmitting coil.

The transmitting coil is supplied with a high frequency AC voltage from roughly 1 to 5000 kHz.

A receiving coil which is located preferably within the transmitting coil is assigned to the latter. The receiving coil has a ratio of the lengthwise dimension to the width dimension (i.e., coil height to coil width) of less than 1 and is preferably less than 0.3, typically even less than 0.2. In particular, the receiving coil can be wound with a not overly large number of turns around a ferromagnetic core with higher relative magnetic permeability, for example, from 10to 10000.

The longitudinal axis of the receiving coil is especially perpendicular to the longitudinal axis of the transmitting coil, the two longitudinal axes having at least roughly one common point or intersection point.

Transmitting and receiving coils form a transformer system with a primary coil and secondary coil which are connected as a (magnetic) flux difference detection arrangement. The transformer interaction between the primary coil and secondary coil is equivalent, i.e., the primary side and secondary side of the transformer system can be interchanged without loss of system function (with consideration of the ratio of number of turns). This arrangement of the transmitting and receiving coils is located within a shielding cup or hollow cylinder with a preferably unilateral opening on its face. The cup is used as the conductor for a magnetic flux and is made of a ferromagnetic material with a relative magnetic permeability greater than 10. The test probe is pivotally mounted relative to an article to be tested and can be turned by a motorized drive with roughly uniform speed around an axis which agrees with an axis of symmetry (especially the longitudinal axis) of the transmitting and receiving coil.

It is advantageous according to the invention if the magnetic shielding cup, at the same time, has electrical shielding made of an electrically conductive material.

One preferred embodiment of the invention comprises an arrangement where the transmitting and receiving coil to be rotated is connected to a rotary transformer provided with an air gap (not to be confused with the aforementioned rotary instrument transformer), so that a transmitting voltage for the transmitting coil and at the same time a receiving voltage produced in the receiving coil can be transmitted without contact.

One economical embodiment with good detection behavior is obtained in accordance with the invention by the receiving coil being designed with a circular cross section and the receiving coil having a rather rectangular cross section. In this way, it is especially easily possible to trace inhomogeneities or defects which are extended in a line and which are located in the vicinity of one edge of an elongated article of electrically conductive material.

According to the invention, it is likewise useful to provide the probe with an additional conventional means with which the average distance of the probe from an article to be tested can be determined so that a signal delivered by the probe becomes essentially independent of distance (so-called distance compensation).

It has been advantageously established that, as the drive for rotation of the probe system, an economical and long-lived commercial three-phase electric motor (induction motor) can be used which runs at a rated speed of roughly 900 to 3600 rpm. Therefore, it is unnecessary to provide specially controlled drive motors for the invention. Instead of an induction motor, other motors can also be used for the invention.

It has been ascertained that, using the features in accordance with the invention, an eddy current test probe for polygonal test specimens can be realized which produces output signals which are essentially independent of which orientation is assumed by the longitudinal axis of a defect relative to the longitudinal axis of a test specimen. In addition, these output signals are even essentially independent of whether these defects are located within a sector which extends to roughly±15° and which is measured around the longitudinal axis of a test specimen. In this case, a reference direction is assumed which is defined by the aforementioned longitudinal axis and an especially rounded edge of the test specimen to be tested.

In another embodiment of the invention, instead of a rotating transmitting coil or receiving coil, a purely electrically working analog is used. For this purpose, there are multiphase transmitting and receiving coil systems formed of a coil set of, for example, 5 coils, and an upstream and downstream electronic phase selection or discrimination stage, so that a motorized drive of the transmitting coil and/or receiving coil can be eliminated. But, for this purpose, the pertinent electronic complexity must be increased. The phase selection system is defined as a system which can electrically connect or activate as the currently chosen coil(s), by means of a selector switch, a number (or a partial number) of several coils or coil sets which point to different azimuth angles. With a phase discrimination system, it is possible to quantitatively determine a proportional, for example, azimuth component, when a magnetic field is present. Therefore, using these known devices and measures, it is possible to generate transmitting rotary fields, or in the peripheral manner, proportional azimuth components of this rotary field.

Overall, the invention is based on the finding that the combination of a transmitting coil and at least one receiving coil leads to essentially better test results, in using a magnetic field for detection of faults in the edge vicinity of a test specimen, if this combination is turned around an axis of symmetry assigned to the two coils. This rotation can be carried out either with mechanical means or by means of an electrically generated rotary magnetic field. One of the longitudinal axes of these coils is preferably perpendicular to the longitudinal axis of a test specimen of elongated shape. Moreover, it is possible to orient one of the longitudinal axes of the coil parallel relative to a surface normal to a test specimen of rather flat shape. The face of one of the participating coils deviates preferably from a circular shape and is stretched longitudinal or ovally, for example. The coil(s) which are used as the receiving coil(s) act typically as a difference sensor for portions of an overall magnetic flux. It is especially economical, according to the invention, to provide a commercial induction AC motor as the rotary drive for the indicated coil combination.

Although it is especially advantageous to operate this invention with eddy current sensors which operate with fixed high frequency flow, the invention can be adapted, in the conventional manner, such that eddy current sensors have one or more frequency-variable oscillators, as modification possibilities, in this respect, are familiar to one skilled in the art.

These and further objects, features and advantages of the present invention will become apparent from the following description when taken in connection with the accompanying drawings which, for purposes of illustration only, show several embodiments in accordance with the present invention.

DETAILED DESCRIPTION OF THE INVENTION

Figure 1:
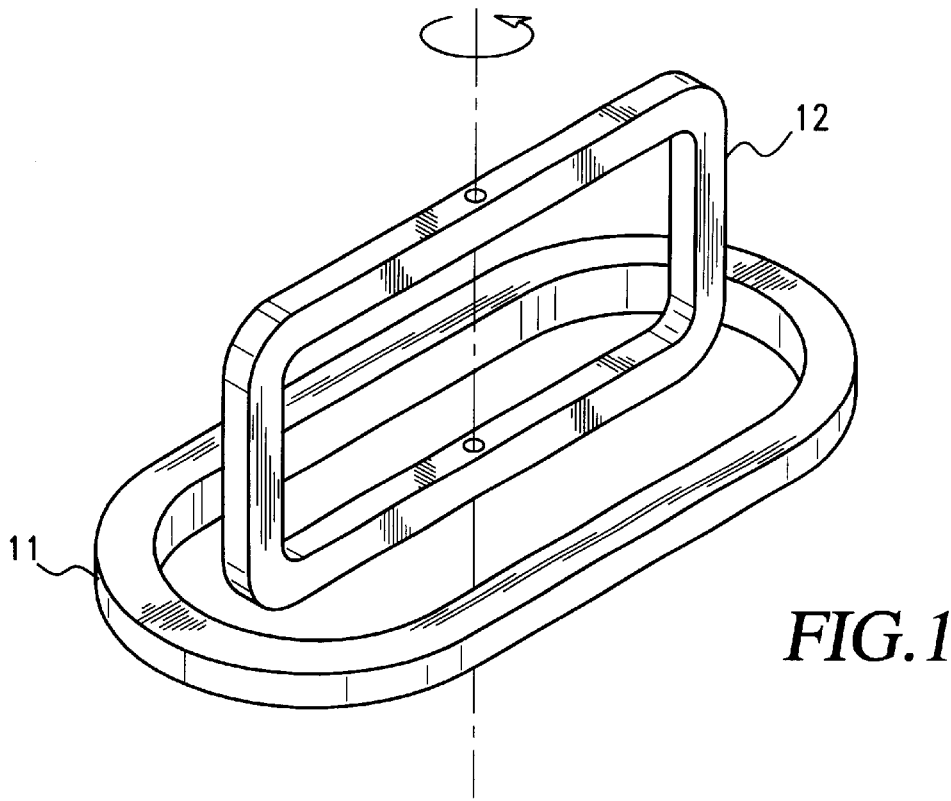
FIG. 1 shows a first basic arrangement of a transmitting and a receiving coil.

A first basic arrangement of a transmitting and receiving coil, as shown in FIG. 1, should be understood as an example in that the two coils represent a transformer unit in which, according to known theorems, what fundamentally matters is which of the two coils is connected as the primary or secondary coil. Normally the coil 11 with a vertical axis and which points preferably at the longitudinal axis of a test specimen is connected as the transmitting coil. The coil 12 which is surrounded by coil 11 is then connected as a receiving coil. The transmitting coil 11 is supplied with high frequency current flow and generates eddy currents in a test specimen. If the specimen is free of defects, essentially no signal is generated in the receiving coil 12 since it only operates when component fluxes of different size from correspondingly symmetrical proportional directions are present. This is always the case when a test specimen to be examined has a mechanical or material-induced defect in the vicinity of the receiving coil. Advantageously, the two coils have a rather small overall height in the direction of their longitudinal axes (field axes). Within the framework of this specification, the longitudinal axis of a coil is always that axis which agrees with the direction of a magnetic field produced by this coil. In addition, at least one of the two coils 11, 12 must have a front face configuration which is of rather elongated or narrow form, and at the same time, it is not of, for example, the quadratic or circular type. It is advantageous if the surrounded inner coil 12 is wound around a ferrite core. As FIG. 1 shows, the coils 11 and 12 are spaced a fixed distance relative to one another. Both are pivotally mounted such that a corresponding axis of rotation runs through the axes of symmetry of the two coils.

Figure 2:
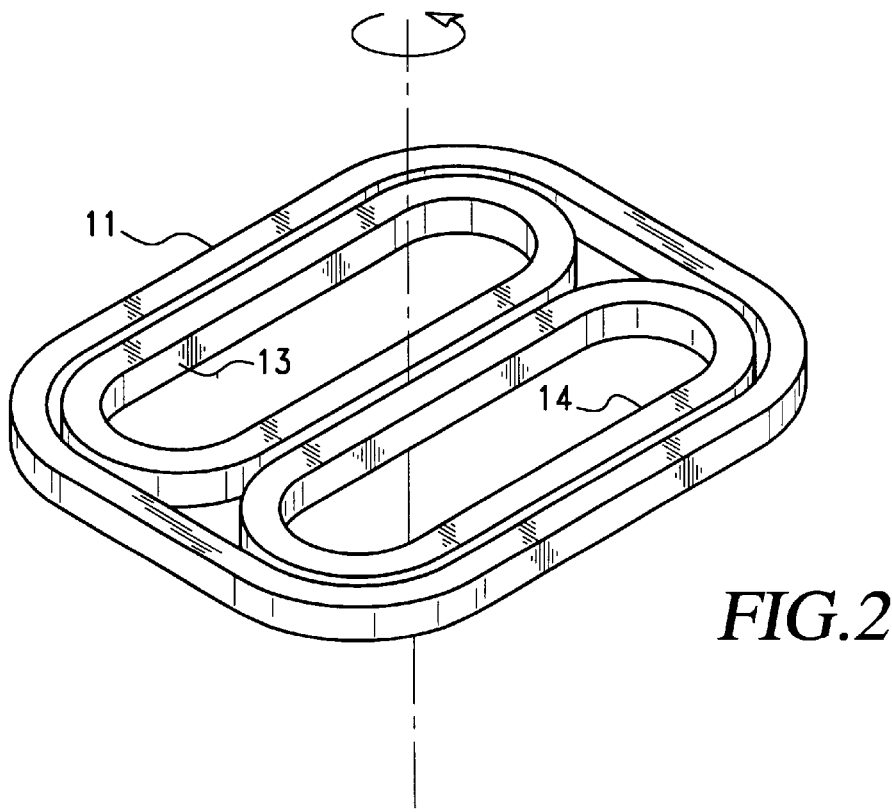
FIG. 2 shows a second basic arrangement of a transmitting and a pertinent receiving coil.

Another fundamental coil arrangement is shown in FIG. 2. Also, this coil arrangement is pivotally mounted around a corresponding axis of rotation symmetrical to the coil arrangement. In contrast to the coil arrangement from FIG. 1, in which the two longitudinal axes of the coils are perpendicular to one another, the longitudinal axes of the coils all run from the transmitting coil 11 and two receiving coils 13, 14 essentially in parallel. As in the preceding case, the coils are more flat than long and of a rather elongated shape with respect to their front face dimensions.

It is not shown in FIGS. 1 & 2 that the participating coils are connected for purposes of supply and removal of high frequency (transmitting and receiving) voltages to one half of a rotary transformer, by which electrical coupling of these voltages to a stationary electrical supply means is possible without slip rings or the like. However, current supply by slip rings is also possible. Furthermore, it is not shown in FIGS. 1 & 2 how the basic coil arrangements are caused to rotate around the indicated axes of rotation by means of an electric motor, for example.

Figure 3:
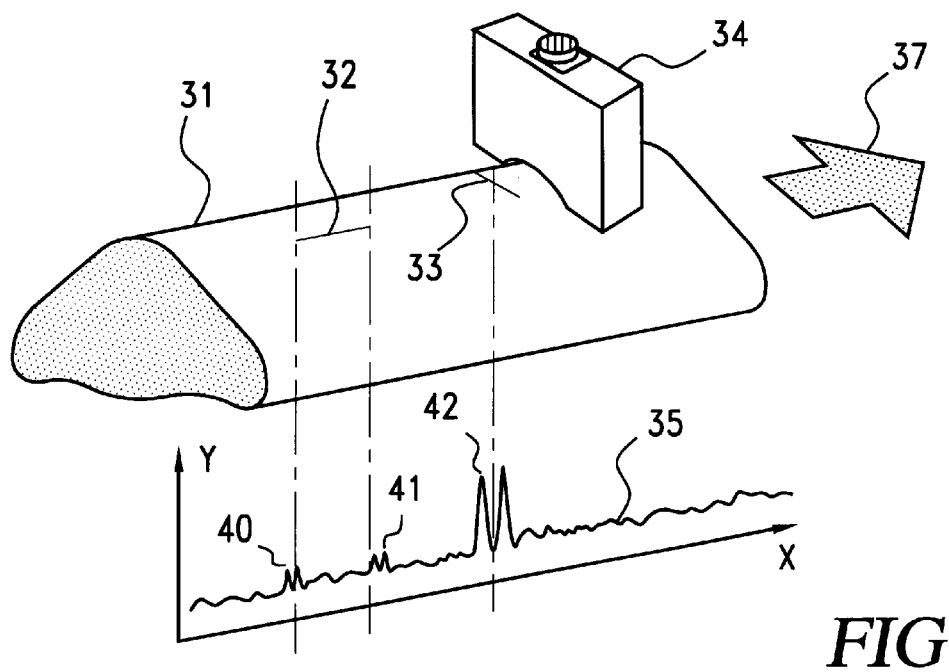
FIG. 3 shows a prior art arrangement for detection of defects in elongated test specimens with polygonal cross section.

FIG. 3 shows an arrangement for detection of defects on elongated test specimens with a polygonal cross section, as is known in the prior art. One such arrangement is located within a housing 34 which is provided with the corresponding electrical terminals and has a probe with a coil set similar to that shown FIGS. 1 or 2, but with the major difference that it is not pivotally mounted. If the corresponding housing, with its active probe in the edge vicinity of a polygonal rod 31, is moved in the direction of the arrow 37, depending on a position x, a measurement signal with an intensity y is recorded, as is shown in the bottom part of FIG. 3. It is shown there how an oblong defect 32 which is oriented essentially in the longitudinal direction of the rod 31 causes only relatively small pulse heights 40 and 41 which are poorly detected relative to background noise 35, 36. Conversely, a similar defect which is oriented essentially in the transverse direction of the rod 31 and which is located, likewise, in the vicinity of a corresponding rod edge produces a much more intense signal 42. Therefore such a signal can be much better detected in devices of the prior art. It is clear that it would be important for purposes of material testing to find comparable detection certainty for both signals.

Figure 4:
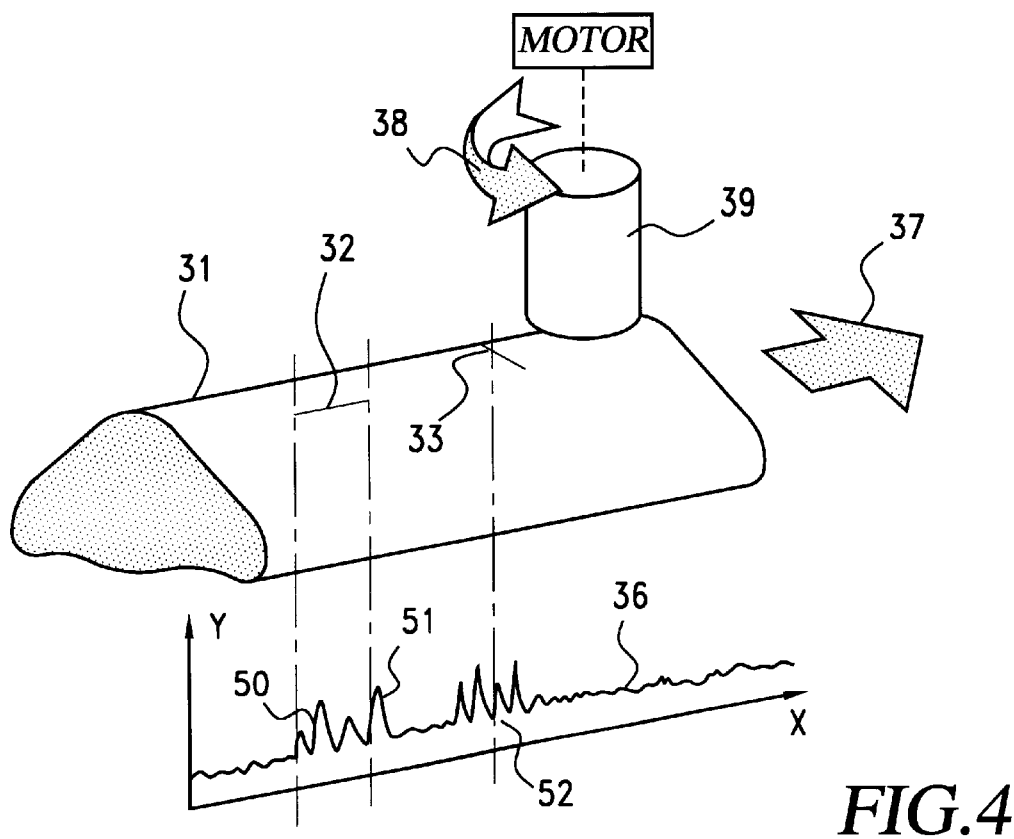
FIG. 4 shows an arrangement in accordance with the invention having rotary coils for detection of defects in elongated test specimens with polygonal cross section.

The solution to this problem is shown in FIG. 4 in which there is likewise a probe which is similar to the one shown in FIG. 3 and described above but which is, however, pivotally mounted in accordance with the invention. An elongated test specimen 31 and one such probe arrangement 39 can be shifted relative to one another, not only linearly (preferably, by transport of the test specimen), but also rotationally (advantageously by rotation of the probe arrangement 39 around the vertical axis, as is shown by arrow 38 in FIG. 4). The orientation of the direction of rotation is used only as an example, since generally the direction of rotation does not matter. The speed with which the probe arrangement 39 is turned is roughly 10 to 100 rps. The rotary drive for the probe arrangement 39 is an electric motor as is only schematically represented. The signals to be supplied to and removed from the probe arrangement 39 can be coupled and decoupled via a rotary transformer (not shown).

To protect against magnetic and electrical problems, the probe arrangement 39 is located in a housing of magnetic and electrically conductive materials. As is shown in FIG. 4, with this probe arrangement, there is a probability for detecting a transversely oriented defect 33, using the generated signal 52, which is much better than for the arrangement shown in FIG. 3. Furthermore, with the device according to the invention, a defect 32 oriented in the longitudinal direction or the direction of travel can be equally well identified using a signal form 50, 51 without changing the measurement means.

Although the test means shown in FIG. 4 is especially well suited to detecting these defects in the vicinity of or on one edge of an elongated polygonal metal piece, the indicated means and the process in accordance with the invention can be used also to advantage in the checking of flat metal (also nonferromagnetic) workpieces.

Figure 5:
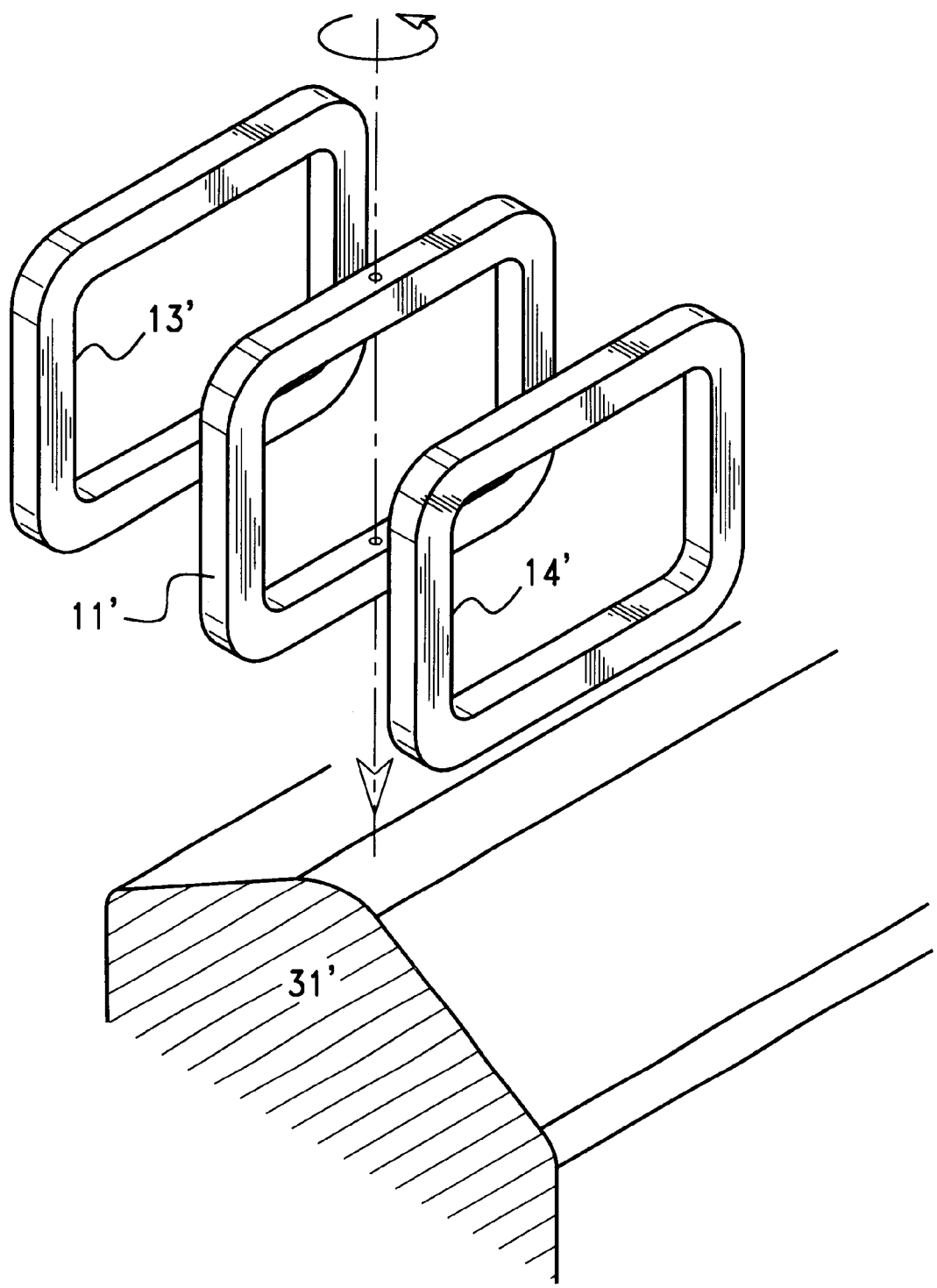
FIG. 5 shows another arrangement according to the invention having rotary coils for detection of defects in elongated test specimens with polygonal cross section.

FIG. 5 shows that, to accomplish the measurement principle of the invention, other coil geometries can be provided so that the longitudinal axes of the coils are oriented perpendicularly to the axis of rotation of the eddy current test probe provided according to the invention, and thus, their longitudinal axes arc not perpendicular to the surface of a test specimen or point to the longitudinal axis of a metal test specimen (for example, a billet or slab). As FIG. 5 shows, the coil arrangement shown there represents a comparably working transformer with which it is possible to determine differences of magnetic (partial) fluxes. The coils can be combined with ferromagnetic cores, flux conductors and similar additional articles in order to better match the arrangement to practical circumstances. In this way, it is possible to modify the type and geometry of a desired magnetic circuit with properties which are also influenced by the local composition of a test specimen to be studied.

FIG, 5. shows that, to accomplish the measurement principle of the invention, other coil geometries can be provided so that the longitudinal axes of the coils are oriented perpendicularly to the axis of rotation of the eddy current test probe provided according to the invention, and thus, their longitudinal axes are not perpendicular to the surface of a test specimen or point to the longitudinal axis of a metal test specimen (for example, a billet or slab). As FIG. 5 shows, the coil arrangement shown there represents a comparably working transformer with which it is possible to determine differences of magnetic (partial) fluxes. The coils 11', 13', and 14' can be combined with ferromagnetic cores, flux conductors and similar additional articles in order to better match the arrangement to practical circumstances. In this way, it is possible to modify the type and geometry of a desired magnetic circuit with properties which are also influenced by the local composition of a test specimen to be studied.

Figure 6:
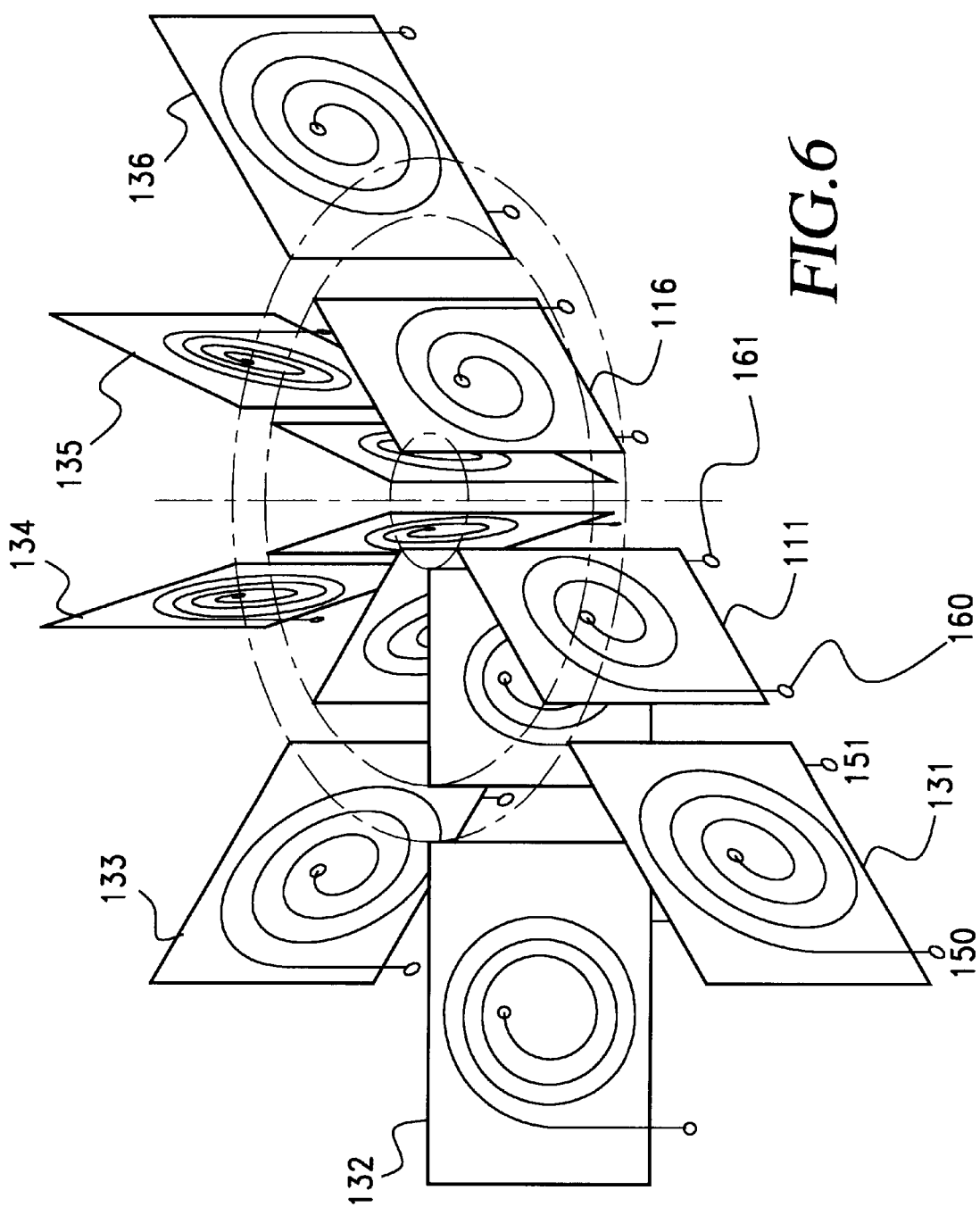
FIG. 6 shows a schematic partial arrangement of coils used for creating a polyphase rotating magnetic field in accordance with a modified embodiment of the invention.

As noted in the "Summary of the Invention" instead of mechanical rotation of the coils being produced, the equivalent result can be achieved by means of an electrically generated rotating magnetic field. FIG. 6 shows an arrangement according to the invention by which a polyphase set of coils can be used for creating such a rotating magnetic field. The set of coils comprise printed circuit coils 131, 132, 133, 134, 135, 136, plus additional sets which have not been shown so as not to affect the clarity of the drawing. These sets of coils will be energized in succession, i.e., one after another, via their terminals 150, 151 etc., by means of an electronic switch (not shown). Thus, a rotating magnetic field will be created, similar to the one generated by the arrangement of coils as shown in FIG. 5. Thus, the sets of coils 111–116 are substituted in place of the central coil 11' depicted in FIG. 5. For this purpose, their respective terminals, e.g., 160, 161 will be connected, in a successive manner, for example, one after another, by means of a second electronic switch (not shown), to an appropriate receiver for evaluating any value of induced voltage in each individual coil, in order to detect induced voltages that differ from an expectation value. Any differing voltage detected indicates an inhomogeneous structure, or a defect, of a probe placed above such sets of coils.

What is claimed is:

1. Eddy current-based test probe for nondestructive material testing and for detecting inhomogeneities or defects of an article of conductive material, with at least one transmitting coil supplied with a high frequency voltage and a receiving coil assigned to it; wherein the receiving coil is located at a fix distance relative to the transmitting coil, has a height to width ratio of less than 1, and a core of a material with magnetic permeability; wherein the at least one transmitting coil has a longitudinal axis and the receiving coil has a longitudinal axis that is oriented substantially perpendicular relative to the longitudinal axis of the at least one transmitting coil, with the longitudinal axes of the receiving and transmitting coils having at least roughly one common intersection point; wherein the transmitting coil and receiving coil are located within a shielding cup with a front face which is produced from a material with magnetic permeability; and wherein the test probe is pivotally mounted and is rotatable around the longitudinal axis of one of the transmitting coil and the receiving coil by a motorized drive.

2. Test probe as claimed in claim 1, wherein the transmitting coil, is located at least in part within the receiving coil.

3. Test probe as claimed in claim 1, in which the shielding cup has electrical shielding of electrically conductive material.

4. Test probe as claimed in claim 1, wherein the transmitting coil has a roughly quadratic cross section and the receiving coil has a narrow, roughly rectangular or elliptical cross section.

5. Test probe as claimed in claim 1, wherein a rotary transformer is provided for transmission of a transmitting voltage for the at least one transmitting coil.

6. Test probe as claimed in claim 1, wherein a rotary transformer is provided for transmission of a receiving voltage produced in the receiving coil.

7. Eddy current-based test probe for nondestructive material testing and for detecting inhomogeneities or defects of an article of conductive material, comprising an essentially coreless transmitting coil within which there is a receiving coil, and a surrounding cup of magnetic and electrically conductive material which is opened on a frontal face in a direction of a test specimen, and wherein an arrangement formed by the coils and cup being rotatable around an axis of the transmitting coil by an electric motor which is used as a rotary drive; wherein a rotary transformer is provided for proximity coupling of electrical signals between said arrangement and a stationary signal generation and evaluation unit; and wherein a means for compensation of signal fluctuations which are caused by a variable average distance of the probe relative to the article of electrically conductive material to be tested is provided.

* * * * *

UNITED STATES PATENT AND TRADEMARK OFFICE
CERTIFICATE OF CORRECTION

PATENT NO.    : 6,377,040 B1  Page 1 of 1
DATED         : April 23, 2002
INVENTOR(S)   : Ludwig Ter Hell It is certified that error appears in the above-identified patent and that said Letters Patent is hereby corrected as shown below:

<u>Title page, Item [54], and Column 1, line 1,</u>
Delete "EDDY CURRENT PROBE AND PROCESS FOR CHECKING THE EDGES OF METAL ARTICLES" add -- EDDY CURRENT TEST PROBE AND PROCESS FOR CHECKING THE EDGES OF METAL ARTICLES --.

Signed and Sealed this

Twenty-first Day of January, 2003

JAMES E. ROGAN
*Director of the United States Patent and Trademark Office*